(12) United States Patent
Welles

(10) Patent No.: US 6,267,721 B1
(45) Date of Patent: Jul. 31, 2001

(54) METHOD AND APPARATUS FOR STRESS RELIEF SYSTEM

(76) Inventor: William F. Welles, 8343 Foothill Blvd., Pine Valley, CA (US) 91962

( * ) Notice: Subject to any disclaimer, the term of this patent is extended or adjusted under 35 U.S.C. 154(b) by 0 days.

(21) Appl. No.: 09/335,969

(22) Filed: Jun. 18, 1999

(51) Int. Cl.[7] .................................................. A61M 21/00
(52) U.S. Cl. ................................ 600/26; 602/45; 602/88
(58) Field of Search .......................... 600/26–28; 607/45, 607/88, 46, 93

(56) References Cited

U.S. PATENT DOCUMENTS

| | | | |
|---|---|---|---|
| 4,315,502 | * | 2/1982 | Gorges ..................................... 600/27 |
| 4,553,534 | * | 11/1985 | Stiegler ................................... 600/28 |
| 4,892,106 | * | 1/1990 | Gleeson, III ........................... 600/28 |
| 5,149,317 | * | 9/1992 | Robinson ............................... 600/27 |
| 5,577,990 | * | 11/1996 | Widjaja et al. ......................... 600/28 |
| 5,643,173 | * | 7/1997 | Welles .................................... 600/26 |

* cited by examiner

Primary Examiner—Samuel G. Gilbert
(74) Attorney, Agent, or Firm—Charles C. Logan, II

(57) ABSTRACT

A stress relief system having a headset to be removably worn on a person's head and a portable electrical wave generator assembly. The left and right speakers of the headset are connected to an electricity powered device for playing recorded music. The electrical wave generator assembly is powered by a 9 volt D.C. battery and it has two closed electrical circuits for transmitting that receive an electrical wave from the electrical wave generator. Each of these circuits has a light emitting diode (LED) that radiates light in the infrared and visible nanometer range. The structure for supporting the respective LED's would be a predetermined length of double stranded wire having sufficient flexibility so that it can be bent to direct the light at preselected points on a patient's hands that are identified by the Koryo Hand Therapy Meridians. A finger loop strap is used to locate and support the lights on the user's fingers.

6 Claims, 4 Drawing Sheets

METHOD AND APPARATUS FOR STRESS RELIEF SYSTEM

BACKGROUND OF THE INVENTION

The invention relates to a method and apparatus for providing stress relief for humans. In industrial nations, the pressure of one's job, the requirement for sufficient money to support one's self and one's family and the desire for material wealth has placed an increased stress level on many individuals. Smoking and drinking alcohol and other vices tend to increase the stress level. Increased stress levels can be harmful to a person's health and can result in heart attacks, strokes and assorted other ailments. Some ways to reduce stress are exercise and meditation.

Traditional American medicine has recently been supplemented with alternative types of treatments. One of the alternative treatments is acupuncture, which is a traditional form of treating people used in the Far East for thousands of years. Books about acupuncture describe numerous meridians that pass through the human body. Along the meridians are points that can be stimulated to promote healthful results.

Three of the meridians that travel along the arm of a person to their head are the triple warmer (TW), the small intestine (SI) and the large intestine (LI) meridians. Each of these meridians has a beginning point (BP) and an end point (EP). These points are also called sing points or acubane points. The reason the triple warmer meridian, the small intestine meridian and the large intestine meridian have special neurological significance is they all begin in the hands and end in the head. The fact that they end in the head means that they have input into the brain or neurology. Any point on these meridians can be used to positive advantage, especially if directed up the head, but for convenience the following points are most important for each meridian.

TW1 and TW23 are the respective beginning and end points on the triple warmer meridian. TW1 (also known as GUANCHONG) is located on the ulnar side of the ring finger, 0.1 cun posterior to the corner of the fingernail. When this acupuncture point is actuated, headaches and hysteria and other symptoms can be alleviated. TW3 (also known as ZHONGZHU) is on the dorsum of the hand between the forth and fifth metacarpal bones. Activation of this point often helps to alleviate headaches. TW23 ends at the end of the eyebrow.

Small intestine point 1 (SI1) is located at the ulnar side of the small finger, about 0.1 cun posterior to the corner of the fingernail. Activation of this point helps to alleviate headaches and other symptoms. The small intestine point 3 (SI3) is located at the end of the transverse crease proximal to the 5th metacarpi-phalangeal joint when the hand is half clinched. Activation of this point helps to alleviate stiffness or rigidity of the neck and also headaches. Small intestine point 19 (SI19) ends in front of the ear.

The large intestine point 1 (LI1) (also known as SHANGYANG) is located on the radial side of the index finger, 0.1 inch posterior to the fingernail. The large intestine point 4 (LI4), (also known as the HEGU), is located on the middle of the second metacarpal bone, on the radial aspect. Actuation of this point alleviates headaches and other symptoms. Large intestine point 20 (LI20) ends lateral to the base of the nose.

Some of the prior art stress control structures and methods are illustrated in U.S. Pat. No. 5,064,410 of Frenkel et al and U.S. Pat. No. 5,242,376 of Shealy et al. The Frankel et al patent uses a pair of eyeglasses having a circuit for monitoring a physiological function of the eyeglass wearer corresponding to a predetermined stress level. The circuit contains an alarm which emits an auditory and/or visual signal in response to a change in said physiological function.

The Shealy et al patent includes a relaxation device that includes a portable mask having a flashing light source. When the mask is positioned on the subjects head a flashing light, having a preselected color is emitted into the subject's eyes. The color is selected to increase beta endorphins into the blood stream of the subject.

Another method and apparatus for stress relief is described in applicant's previous U.S. Pat. No. 5,643,173. It has a square wave generator that is connected to two separate closed circuits each having a light emitting diode at their ends. Each of these circuits has a human body ground member electrically connected to the wave generator. When the respective human body ground members are in contact with the human body, the square wave electrical signal will pass through the person's body between the respective human ground members. In a second embodiment, the human ground member is the temple member of an eyeglass frame.

It is an object of the invention to provide a novel method and apparatus that is for stress relief that does not require the electrical circuits to use the human body as a ground.

It is also an object of the invention to provide a novel method and apparatus for stress relief that has been designed to function on a patient's hands where the points are on the Koryo Hand Therapy Meridians.

It is another object of the invention to provide a novel method and apparatus for stress relief that utilizes Koryo Hand Therapy meridians that are approximately three times as powerful as the conventional acupuncture point of the body utilized by U.S. Pat. No. 5,643,173.

It is an additional object of the invention to provide a novel method and apparatus for stress relief that is portable and easily used by a patient.

It is a further object of the invention to provide a novel method and apparatus for stress relief that doesn't introduce electricity into the body. Electricity introduced into the body has disadvantages (i.e. for pacemakers in the heart).

SUMMARY OF THE INVENTION

The invention relates broadly to the field of systems and machines that employ minute illumination impulses for stimulating or inducing therapeutic action for health minded individuals.

In using the stress relief system, the electrical wave generator assembly would have the male terminal of the flexible wire inserted into the output jack of the electrical wave generator assembly housing. The free ends of the wires would have their respective finger loop straps secured to the respective left and right ring fingers of the patient's hands. The LED's would be positioned where they direct their light rays either on the triple warmer, small intestine, or large intestine points as they are identified on the Koryo Hand Therapy Meridian chart. The most effective points are L3, H3 and D3. These are source points and are effective for balancing the energy of the micro meridians. The headset would be placed on the patient's head. Concurrently, the switch on the wave generator housing would be actuated along with turning on the switch of the CD player. The light rays from the LED's stimulate the micromeridian points on the patient's hands and seem to resonate into the person's mind to allow a state of ease and relaxation to come over the body. At this same time the music on the CD disk will be transmitting sound to the patient's left and right ears. on the (H) small intestine meridian the primary statement used is "I deeply accept myself just the way I am" or "I deeply accept myself in spite of . . . . The inputing of self-acceptance allows past trauma of all sorts to be released by the individual. The technique used for this is based on the work of Roger Callahan, Phd.

Using the (L) Triple Heater meridian allows the brain to be more directly accessed. People can think of a memory while the light is on L3 and they circle their eyes, hum or count. These techniques help clear the memory.

Another novel application of this product and the (L) or Triple Heater meridian is to establish a whole brain connection. The technique involves having the light on (L3) while the individual anchors his fingers in his ears with his index fingers and alternatively taps the temporal region of the head with the middle finger and then taps the thumb with the middle finger (See FIG. 4). This tapping is accompanied with circling the eyes and walking in place with or without the music. This technique establishes whole brain connections. Once the brain is whole and connected this connectiveness can be built on by stressing the body that is dis-connected in any way and then tapping as described before. This technique of stressing and reconnecting by tapping can be demonstrated effective by checking and rechecking muscle strengths before and after the tapping. A weak muscle that is created after stressing that becomes strong after tapping is evidence of a neural re-connection.

Other statements such as those below would be received from the CD player: (1) I let go of all anxiety worry and fear and take in peace, rest, and calm, (2) I want to be 100% healthy on all levels, (3) it is all right if I am 100% healthy, (4) it is safe to be 100% healthy on all levels, (5) I deserve to be 100% healthy on all levels, (6) It is okay to be 100% healthy on all levels, etc.

By repeating these statements while having the light input from the LED's, these statements quickly become congruous with the belief nature of the individual. Statements 2–6 above fall into a category of statements of incongruence with health that are called reversals. Reversals are negative reverse beliefs that we hold onto to the detriment of our mental and physical health.

The symptoms of headaches, irritability, and blurring vision associated with the aforementioned micromeridians are definitely mental symptoms which is why stimulating these micromeridian points in combination with voice reinforcement, seem to have a synergistic effect to work most effectual for clearing stress and negative mental beliefs.

DESCRIPTION OF THE PREFERRED EMBODIMENT

Figure 1:
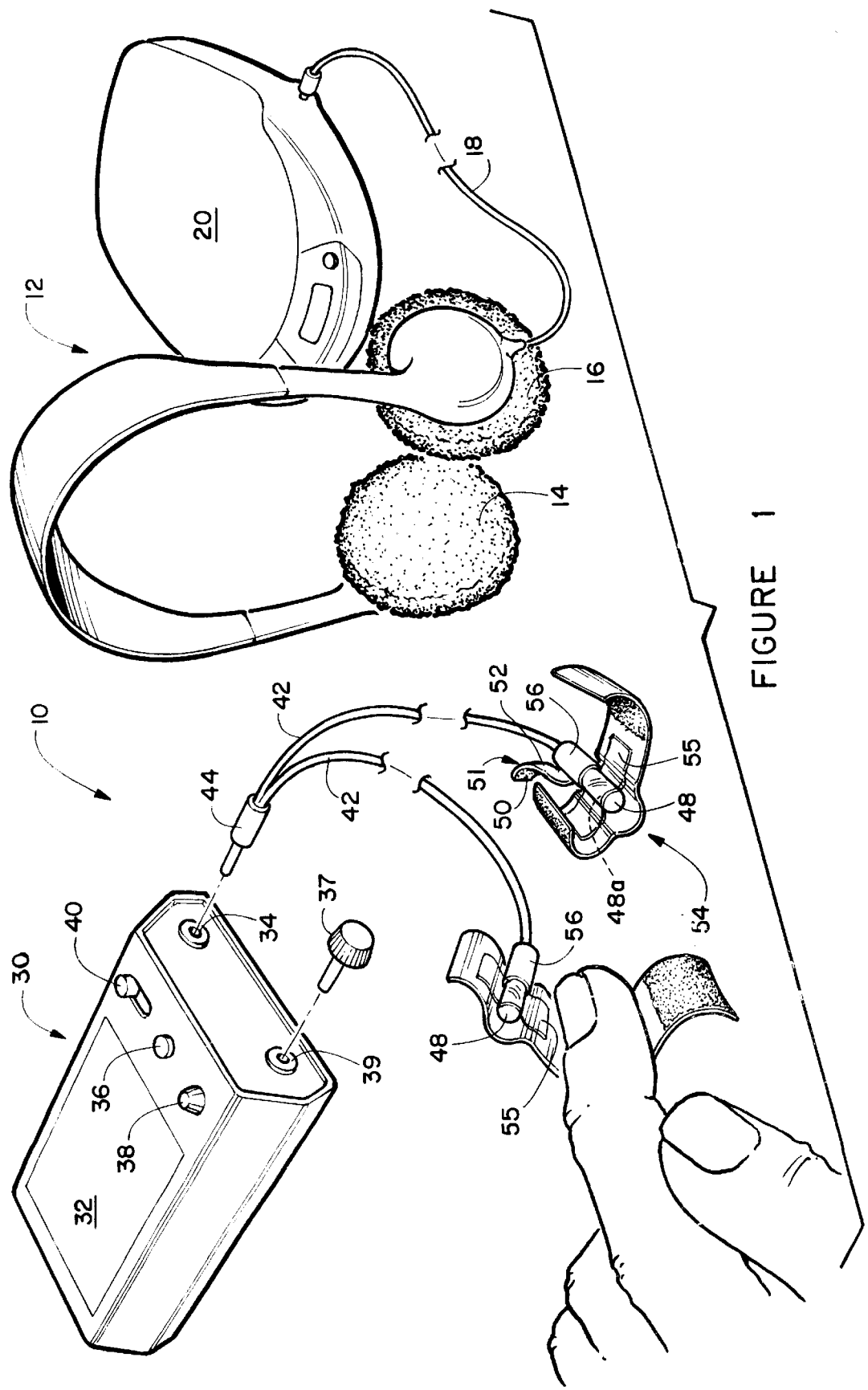
FIG. 1 is an exploded front perspective view of the components of the novel stress relief apparatus.

The novel stress relief system will now be described by referring to FIGS. 1–3 of the drawings. The stress relief apparatus is generally designated numeral 10. A second major component of the system is the headset 12. Headset 12 has a left ear speaker 14 and a right ear speaker 16. An electrical wire 18 connects headset 12 to an electric powered device for playing a recorded music, such as a CD player 20.

Electrical wave generator assembly 30 has a housing 32 with output jacks 34 and 36. A pair of LED's each having a body portion 48a are illuminated when switch 40 is actuated. A pair of electric conductor wires 42 have a male terminal 44 on one end that is detachably inserted into output jack 34. The conductor wires 42 have a length L1 that is in the range of 24 to 56 inches. Electrical wires 42 each make a closed loop circuit with a red light emitting LED 48 at each of their outer ends. LED 48 emits light only in the infrared and visible light spectrum range. Knob 37 is used to adjust the frequency of the flashing lights and it is detachably inserted into socket 39.

Wires 42 have a tubular sleeve 56 on them adjacent LED 48. A Velcro attachment tab 51 has a front end 50 and a rear end 52. Rear end 52 is secured to tubular sleeve 56. Finger loop straps 54 have an alignment sleeve 55 secured to their inner surface for removably receiving the LED's 48 and keep them aligned on the respective X-axes. Velcro tab 51 is pressed against Velcro material on the outer surface of finger loop straps 54 to hold the LED's 48 in alignment sleeves 55.

Figure 2:
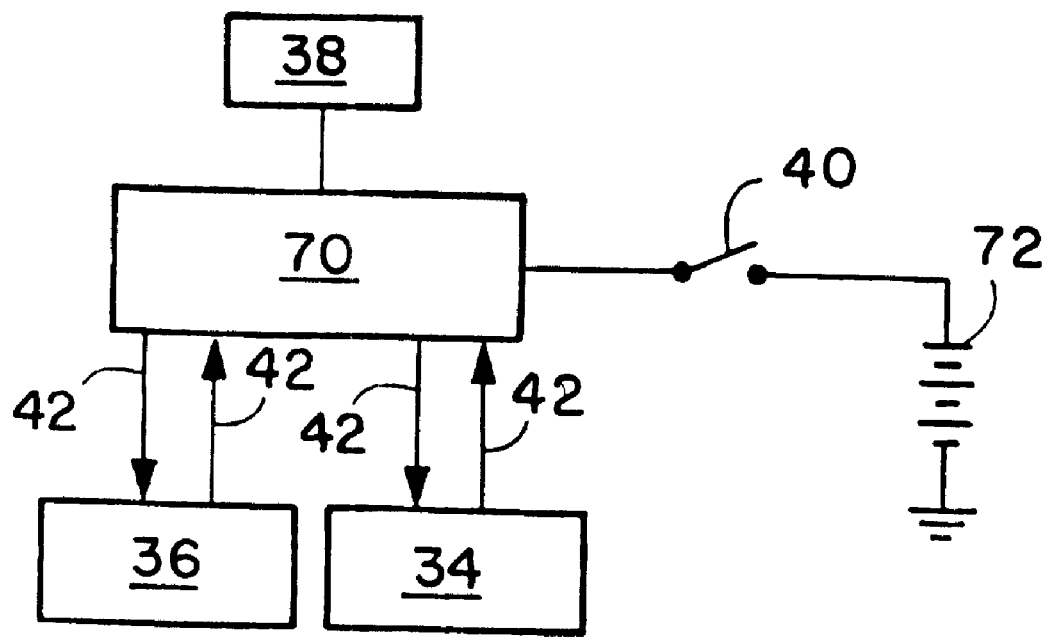
FIG. 2 is a schematic electrical diagram of the electrical wave generator assembly circuit.

FIG. 2 illustrates a schematic diagram of the electrical circuit of the electrical wave generator assembly 30. It has a PC board 70 having an electrical wave generator circuit mounted thereon that is powered by a 9 volt DC battery 72. The electrical wave pattern can be varied from a frequency range of 2 cycles per second to 200 KHZ per second and still be effective. Output jacks 34 and 36 are electrically connected to circuit board 70. Male terminal 44 is detachably inserted into output socket 34 to provide current for the two LED's 48. A potentiometer (not shown) could be plugged into output socket 36 in order to vary the shape of the electrical wave. A knob 37 is shown plugged into output socket 39 in order to vary the frequency of the flashing lights.

Figure 3:
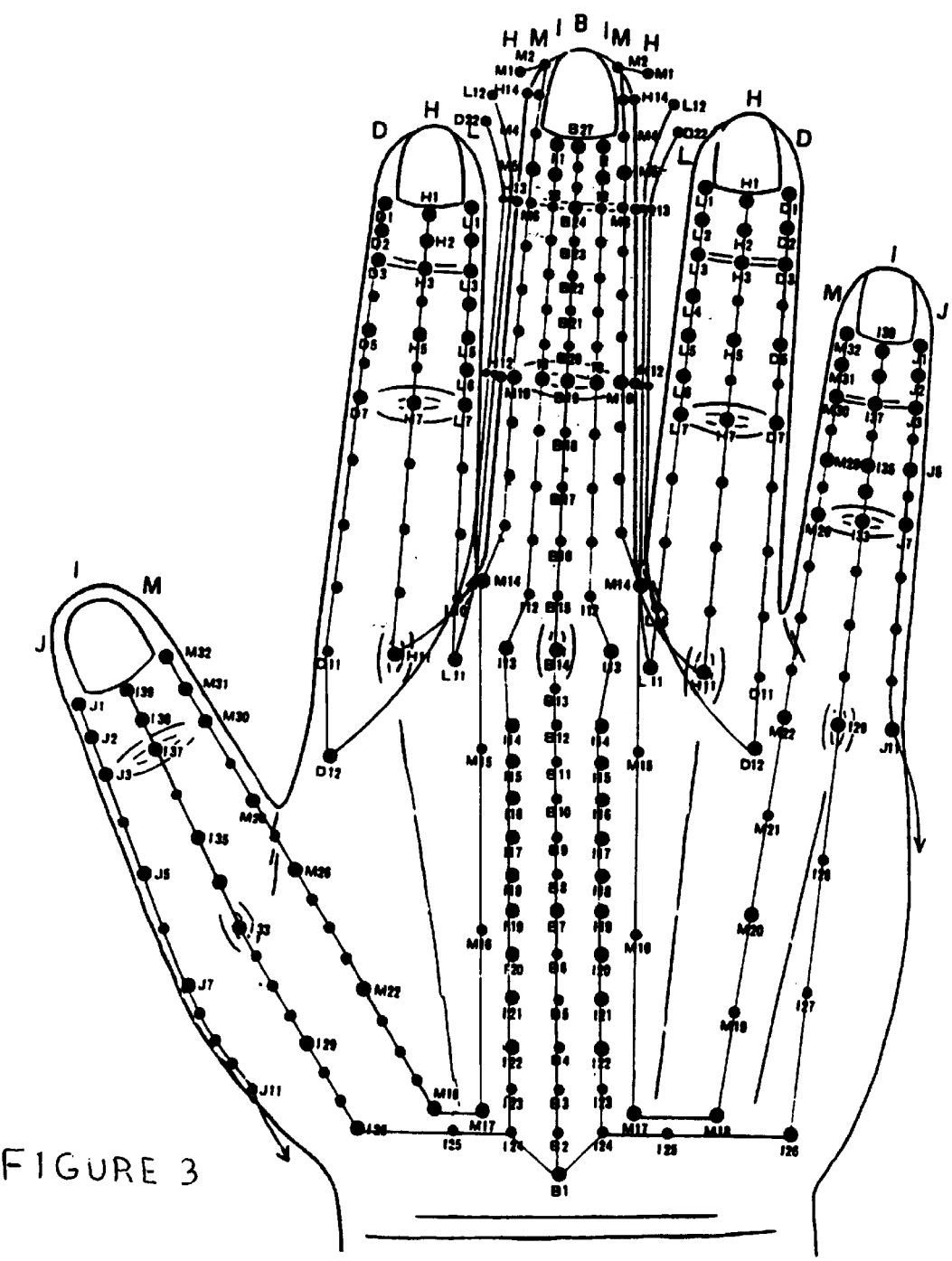
FIG. 3 illustrates the Koryo Hand Therapy Meridians of a hand.

FIG. 3 illustrates the Koryo Hand Therapy Meridians. The L (Triple Warmer), H (Small Intestine) and D (Large Intestine) all begin on the hand and end in the head. The end digit of the ring finger is analogous to the hand and the end digit of the middle finger is analogous to the head. These micromeridian points from the Koryo chart are approximately three times more powerful than traditional acupuncture points because the hand has huge representation in the brain mapping (homongulous). Because of the fact these points have huge representation in the brain, it is possible to accomplish more with less stimulation. Thus only light stimulation of acupuncture points on L (Triple Warmer) H (Small Intestine), and D (Large Intestine) combined with sound stimulation through the ears or a piezo electric transducer right on the skin. Light stimulation of the L,H,D micromeridians with sound stimulation of the brain accomplishes a synergism that allows statements such as "I deeply accept myself" to be received more readily by the body. The sound therapy we feel is stimulating the hypothalamus or the brain body interface. Sounds that work best are high frequency sounds or pieces of music with high frequency sounds.

Figure 4:
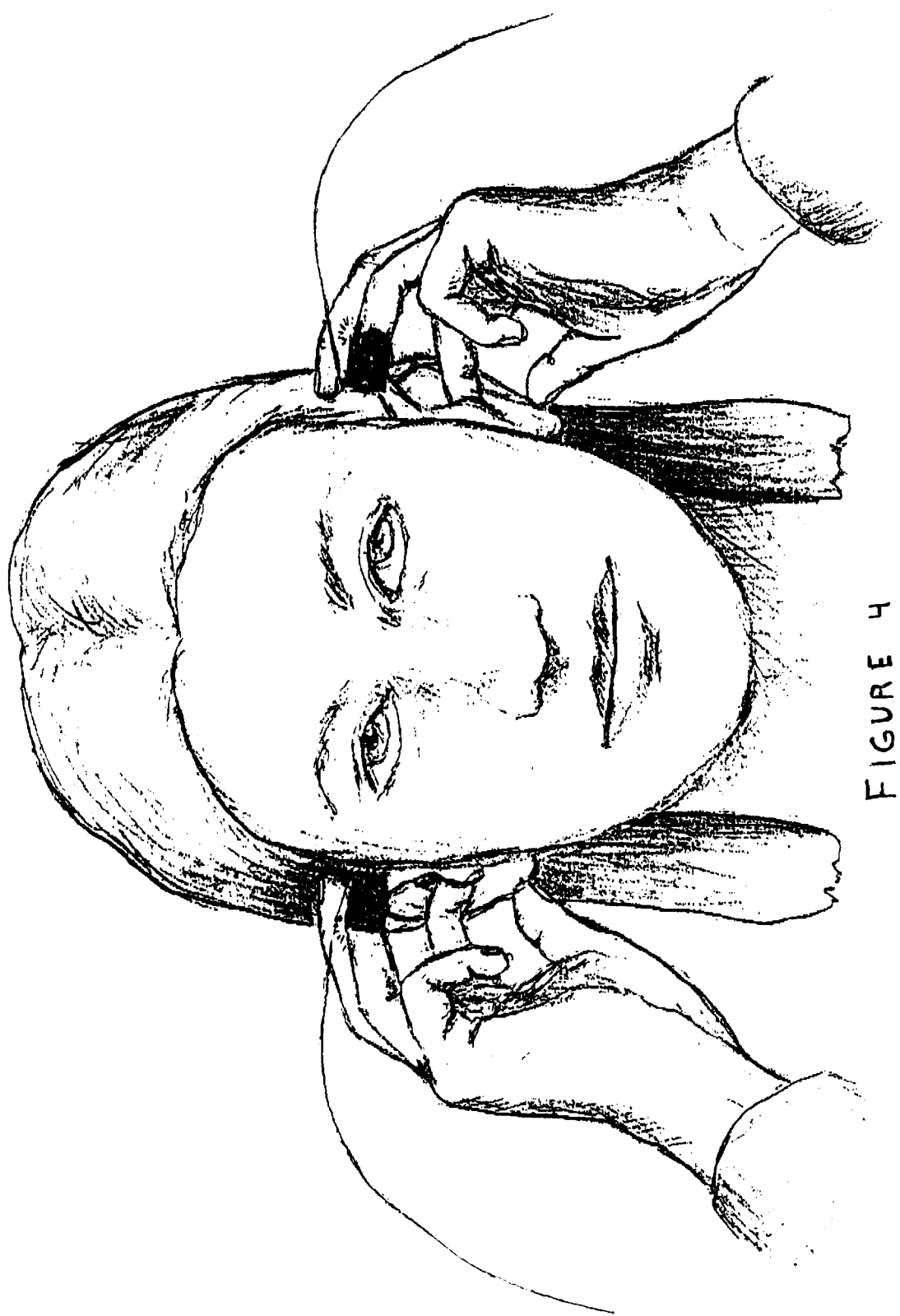
FIG. 4 illustrates a person using the finger loop straps on her ring fingers to establish a whole brain connection.

FIG. 4 also illustrates a person using the finger loop straps 54 on their ring fingers to establish a whole brain connection.

What is claimed is:

1. The stress relief system comprising:
    an electrical wave generator assembly having means for emitting an electrical wave pattern in the 2 cycles per second to 200 KHZ cycles per second range; said electrical wave generator assembly having a housing with an output jack;

a source of electrical power connected to said electrical wave generator assembly;

a first elongated light emitting diode (LED) having a front end, a rear end, a body portion, an elongated first tubular sleeve connected to said rear end of said first LED; said first tubular sleeve having an outer diameter greater than the outer diameter of said first elongated LED to form a shoulder at their juncture;

first closed loop electrical circuit having a front end for transmitting an electrical current from said output jack of said electrical wave generator to said rear end of said first LED and back to said output jack; said first closed loop electrical circuit having a preselected length L1;

a transversely extending first finger loop strap having a first end, a second end, an outer surface and an inner surface; a longitudinally extending elongated first alignment sleeve having a front end and a rear end is secured to said inner surface of said first finger loop strap; said first alignment sleeve removably receiving said body of said first LED until said rear end of said first alignment sleeve rests against said shoulder of said first tubular sleeve; first hook and loop fastening means on said first and second ends of said first finger loop strap for removably attaching said first loop fastening means to a patient's finger; a first elongated attachment tab having a front end, a rear end, attached to said first tubular sleeve; and a second hook and loop fastening means located adjacent said front end of said first elongated attachment tab that is detachably secured to said first hook and loop fastening means on said first finger loop strap for preventing said first LED from pulling out of said alignment sleeve;

a second elongated light emitting diode (LED) having a front end, a rear end, a body portion, an elongated second tubular sleeve connected to said rear end of said second LED; said second tubular sleeve having an outer diameter greater than the outer diameter of said second elongated LED to form a shoulder at their juncture;

a second closed loop electrical circuit having a front end for transmitting an electrical current from said output jack of said electrical wave generator to said rear end of said second LED and back to said output jack; said second closed loop electrical circuit having a preselected length L1;

a transversely extending second finger loop strap having a first end, a second end, an outer surface and an inner surface; a longitudinally extending elongated second alignment sleeve having a front end and a rear end is secured to said inner surface of said second finger loop strap; said second alignment sleeve removably receiving said body of said second LED until said rear end of said second alignment sleeve rests against said shoulder of said second tubular sleeve; third hook and loop fastening means on said first and second ends of said second finger loop strap for removably attaching said second loop fastening means to a patient's finger; a second elongated attachment tab having a front end, a rear end, attached to said first tubular sleeve; and a second hook and loop fastening means located adjacent said front end that is detachably secured to said first hook and loop fastening means on said first finger loop strap for preventing said first LED from pulling out of said alignment sleeve; and a head set having a left ear speaker and a right ear speaker; said head set adapted to be worn on a person's head; an electrically powered device for playing recorded songs; and means for electrically connecting said electrically power device to said speaker of said head set.

2. A stress relief system as recited in claim 1 wherein said source of electrical power is a battery.

3. A stress relief system as recited in claim 2 wherein said battery is a 9 volt D.C. battery.

4. A stress relief system as recited in claim 1 wherein said first and second LED's are unidirectional lights.

5. A stress relief system as recited in claim 1 wherein said LED's are red light emitting LED's.

6. A method for reducing the stress level of a patient comprising the steps of:

a) connecting an electrical wave generator assembly to a first closed loop electrical circuit for transmitting an electrical current to a first LED that only emits an electrical wave pattern in the 2 cycles per second to 200 KHZ cycles per second range; said first closed loop electrical circuit being entire outside the body of said patient; a transversely extending first finger loop strap having a first end, a second end, an outer surface and an inner surface; a longitudinally extending elongated first alignment sleeve having a front end and a rear end is secured to said inner surface of said first finger loop strap; said first alignment sleeve removably receiving said body of said first LED until said rear end of said first alignment sleeve rests against said shoulder of said first tubular sleeve; first hook and loop fastening means on said first and second ends of said first finger loop strap for removably attaching said first loop fastening means to a patient's finger; a first elongated attachment tab having a front end, a rear end attached to said first tubular sleeve; and a second hook and loop fastening means located adjacent said front end of said first tubular sleeve that is detachably secured to said first hook and loop fastening means on said first finger loop strap for preventing said first LED from pulling out of said first alignment sleeve;

b) connecting an electrical wave generator assembly to a second closed loop electrical circuit for transmitting an electrical current to a second LED that only emits an electrical wave pattern in the 2 cycles per second to 200 KHZ cycles per second range; said second closed loop electrical circuit being entire outside the body of said patient; a transversely extending second finger loop strap having a first end, a second end, an outer surface and an inner surface; a longitudinally extending elongated second alignment sleeve having a front end and a rear end is secured to said inner surface of said second finger loop strap; said second alignment sleeve removably receiving said body of said second LED until said rear end of said second alignment sleeve rests against said shoulder of said second tubular sleeve; third hook and loop fastening means on said first and second ends of said second finger loop strap for removably attaching said first loop fastening means to a patient's finger; a second elongated attachment tab having a front end, a rear end, attached to said second tubular sleeve; and a fourth hook and loop fastening means located adjacent said front end of said second tubular sleeve that is detachably secured to said third hook and loop fastening means on said first finger loop strap for preventing said second LED from pulling out of said second alignment sleeve;

c) directing said first LED and said second LED at preselected Koryo Hand Therapy Meridian points on the hand's of a patient;

d) placing a headset on the head of a patient with the left and right speakers of the headset being positioned on the ears of a patient; said headset being connected to an electrically powered device for playing recorded music;

e) turning on the power of the electrically powered device for playing recorded music so that a patient hears the music; and f) turning on the power of the electrical wave generator to send electrical current to said first and second LED's causing them to emit an electrical wave pattern in the 2 cycles to 200 KHZ cycles per second range at the preselected points on the Koryo Hand Therapy Meridian points of a patient's hands to reduce their stress level.

\* \* \* \* \*